US008815284B2

(12) United States Patent
Guo et al.

(10) Patent No.: US 8,815,284 B2
(45) Date of Patent: Aug. 26, 2014

(54) BIOERODIBLE SUSTAINED RELEASE DRUG DELIVERY SYSTEMS

(75) Inventors: Hong Guo, Belmont, MA (US); Jianbing Chen, Belmont, MA (US); Dongling Su, Franklin, MA (US); Paul Ashton, Boston, MA (US)

(73) Assignee: pSivida US, Inc., Watertown, MA (US)

( * ) Notice: Subject to any disclaimer, the term of this patent is extended or adjusted under 35 U.S.C. 154(b) by 1570 days.

(21) Appl. No.: 10/877,761

(22) Filed: Jun. 25, 2004

(65) Prior Publication Data

US 2005/0025834 A1 Feb. 3, 2005

Related U.S. Application Data

(60) Provisional application No. 60/483,316, filed on Jun. 26, 2003, provisional application No. 60/501,947, filed on Sep. 11, 2003, provisional application No. 60/575,307, filed on May 28, 2004.

(51) Int. Cl.
*A61K 9/66* (2006.01)

(52) U.S. Cl.
USPC .............................. 424/455; 424/451; 424/463

(58) Field of Classification Search
USPC .................................. 424/426, 463, 454, 459
See application file for complete search history.

(56) References Cited

U.S. PATENT DOCUMENTS

| 5,324,280 | A | | 6/1994 | Wong et al. |
| 5,324,519 | A | | 6/1994 | Dunn et al. |
| 5,378,475 | A | | 1/1995 | Smith et al. |
| 5,516,527 | A | | 5/1996 | Curatolo |
| 5,618,560 | A | * | 4/1997 | Bar-Shalom et al. ......... 424/486 |
| 5,681,964 | A | | 10/1997 | Ashton et al. |
| 5,736,152 | A | | 4/1998 | Dunn |
| 5,744,153 | A | | 4/1998 | Yewey et al. |
| 6,156,764 | A | | 12/2000 | Asmussen et al. |
| 6,375,972 | B1 | | 4/2002 | Guo et al. |
| 2003/0082234 | A1 | | 5/2003 | Seo et al. |

FOREIGN PATENT DOCUMENTS

| CA | 2283939 | | 9/1998 |
| CA | 2394716 | | 7/2001 |
| CA | 2473526 | | 7/2003 |
| JP | 2229110 | A | 9/1990 |
| JP | 5305135 | A | 11/1993 |
| WO | WO-97/26015 | | 7/1997 |
| WO | WO-00/35419 | | 6/2000 |
| WO | WO-02/00137 | | 1/2002 |
| WO | WO-02/36169 | A2 | 5/2002 |
| WO | WO-02/45689 | A1 | 6/2002 |
| WO | WO-02/49573 | A2 | 6/2002 |

OTHER PUBLICATIONS

Editions Du Vidal Ed.—Editions Du Vidal: "Vidal 1997", Dictionnaire Vidal 1997, Paris, Editions Du Vidal, Fr, Neoral, XP002334163.
Jain, R.A., et al; "Controlled delivery of drugs from a novel injectable in situ formed biodegradable PLGA microsphere system"; Journal of Microencapsulation, Taylor and Francis Inc., London, GB; vol. 17, No. 3, May 2000; pp. 343-362; XP-000912452; ISSN: 0265-2048.
International Search Report for PCT/US2004/020369 dated Jan. 17, 2005.
ROC (Taiwan) Search Report dated Mar. 3, 2010 for Patent Application No. 093118702.

* cited by examiner

*Primary Examiner* — James Rogers
(74) *Attorney, Agent, or Firm* — Foley Hoag LLP

(57) ABSTRACT

The present invention relates to sustained release drug delivery systems, medical devices incorporating said systems, and methods of use and manufacture thereof. The inventive systems feature bioerodible drug delivery devices that include biocompatible solid and biocompatible fluid compositions to achieve desired sustained release drug delivery.

23 Claims, 1 Drawing Sheet

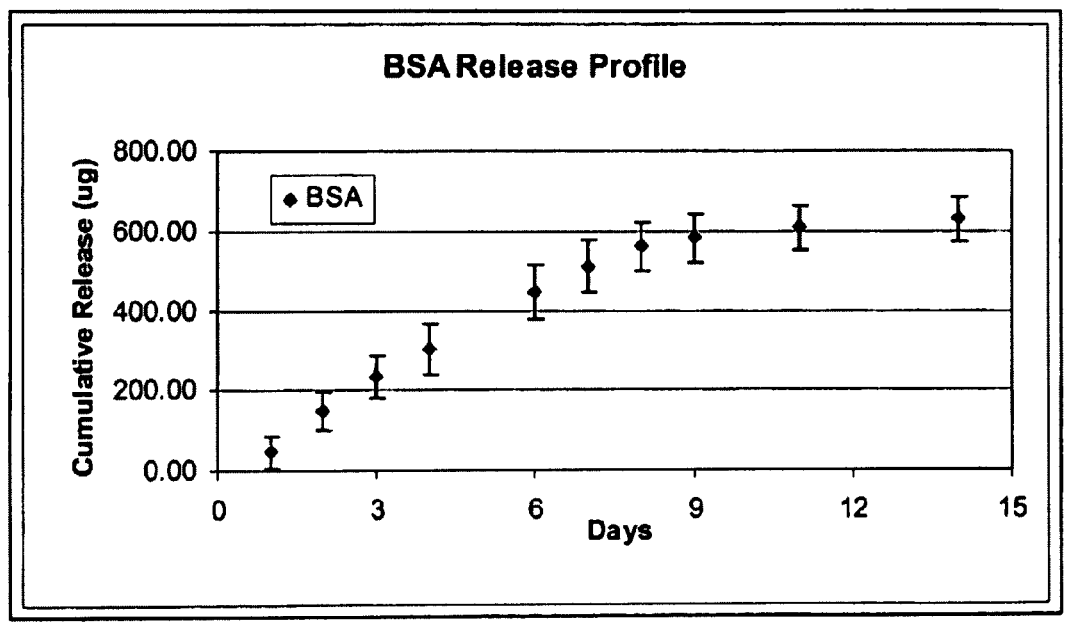

BIOERODIBLE SUSTAINED RELEASE DRUG DELIVERY SYSTEMS

RELATED APPLICATIONS

This application claims the benefit of U.S. provisional application 60/483316, filed Jun. 26, 2003, U.S. provisional application 60/501947, filed Sep. 11, 2003, and U.S. provisional application 60/575307, filed May 28, 2004, the specifications of which are incorporated by reference herein.

BACKGROUND OF THE INVENTION

Numerous techniques and systems have been developed to enhance drug delivery. A principal objective is to provide the sustained release of a drug under conditions that allow sufficient control over the drug's delivery rate. Some systems employ a polymer drug delivery device in search of such control, while others achieve sustained release by temporarily altering the chemical properties of the agent or packaging the agent with excipients or other agents. Nevertheless, systems are needed that allow for improved control of drug delivery.

BRIEF DESCRIPTION OF THE FIGURES

FIG. 1 depicts the release of bovine serum albumin ("BSA-")from a semi-solid gel formed from BSA and PLGA-PEG in a sealed silicone cup with a small hole into 0.1 M phosphate buffer, pH 7.4, as monitored by HPLC.

SUMMARY OF THE INVENTION

The present invention relates to sustained release drug delivery systems featuring polymer drug delivery devices that include biocompatible fluid and biocompatible solid core components, where the biocompatible solid is less soluble in physiological fluid than in the biocompatible fluid. The systems allow desired sustained release drug delivery. The invention also contemplates medical devices employing such systems, and methods of use thereof.

DETAILED DESCRIPTION OF THE INVENTION

The invention provides a polymer drug delivery system ("polymer system") comprising an inner core or reservoir that contains a therapeutically effective amount of an agent, a first coating layer that is impermeable, negligibly or partially permeable to the agent and, optionally, a second coating layer that is permeable or semi-permeable to the agent. Additional layers may also optionally be used.

The inner core has biocompatible fluid and biocompatible solid components, where the biocompatible solid is less soluble in physiological fluid than in the biocompatible fluid. The biocompatible fluid may be hydrophilic, hydrophobic or amphiphilic; and may be polymeric or nonpolymeric. Such fluid may also be a biocompatible oil (such as sesame oil, miglyol, or the like). In certain embodiments, a biocompatible solid (e.g., a bioerodible polymer) is dissolved, suspended, or dispersed in the biocompatible fluid (to form a "biocompatible core component"). In certain embodiments, at least one agent is also dispersed, suspended, or dissolved in the biocompatible core component. In certain embodiments, an agent is dissolved in the biocompatible fluid. In certain embodiments, the biocompatible fluid is a liquid agent that, when combined with a biocompatible solid, is in a form suitable for injection.

In certain embodiments, the inner core has biocompatible fluid and biocompatible solid components, wherein the biocompatible fluid component is a liquid drug or includes a liquid with a drug dissolved therein, and the biocompatible solid component is dissolved, suspended, or dispersed in the liquid drug to form a biocompatible core component. Other drugs or agents may, but need not, be dispersed, suspended, or dissolved in the biocompatible core component.

The first coating layer surrounds the inner core, is an impermeable, negligibly or partially permeable polymer, and may feature one or more diffusion ports or pores ("pores") that further allow the drug to diffuse from the core out of the system. The rate of drug release from such systems may be controlled by the permeability of the agent in the core, the solubility of the agent in the biocompatible core component, the thermodynamic activity of the agent in the biocompatible core component, the potential gradient of the agent from the core to surrounding physiological fluid, the size of the diffusion pore(s), and/or the permeability of the first or additional coating layer(s). In certain embodiments, the coating layer(s) is bioerodible, while in other embodiments it is non-bioerodible.

U.S. Pat. Nos. 5,378,475, 5,773,019, 5,902,598, 6,001,386, and 6,375,972, as well as co-pending U.S. patent applications Ser. Nos. 10/428,214 and 60/501947 disclose various embodiments of sustained release drug delivery systems with one or more polymer coating layers. By way of illustration and not limitation, such devices may be usefully employed with the systems described herein, and the entire disclosures of those references are incorporated herein by reference.

In preferred embodiments, the first coating layer includes at least one polymer (and may, optionally, include more than one polymer), and is preferably bioerodible, but may alternatively be non-bioerodible. The first coating layer covers at least part but preferably not all of the surface of the inner core, leaving at least one diffusion pore through which the agent can pass from the inner core. In certain embodiments, particularly where impermeable, the membrane may have one or more pores. If a second layer is used, it may partially cover or cover essentially all of the first coating layer and inner core, and its permeability to the agent permits the agent to diffuse into the surrounding fluid.

A variety of polymers may be suitable to form the coating layer(s) of the present invention. Preferable polymers are largely insoluble in physiological fluids. Suitable polymers may include naturally occurring or synthetic polymers. Certain exemplary polymers include, but are not limited to, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene chlorinated polyethylene, poly(1,4-isopropylidene diphenylene carbonate), vinylidene chloride, acrylonitrile copolymer, vinyl-chloride-diethyl fumarate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, vinyl chloride-acrylonitride copolymer, etc.

The biocompatible core component includes at least one biocompatible solid (e.g., a bioerodible polymer) that is at least partially dissolved, suspended, or dispersed in a biocompatible polymeric or nonpolymeric fluid or a biocompatible oil. Further, the biocompatible solid is more soluble in the biocompatible fluid or oil than in immediately surrounding physiological fluid such that, when the device is placed in contact with physiological fluid, the biocompatible core component precipitates or undergoes a phase transition. The inner core may be delivered as a gel. It may preferably be delivered as a particulate or a liquid that converts to a gel upon contact with water or physiological fluid. In some embodiments, the biocompatible (e.g., nonpolymeric) fluid may include a drug in free base form.

In certain embodiments, the biocompatible fluid of the biocompatible core component is hydrophilic (e.g., PEG, cremophor, polypropylene glycol, glycerol monooleate, and the like), hydrophobic, or amphiphilic. In certain embodiments, said fluid may be a monomer, polymer or a mixture of the same. If used, the biocompatible oil may be sesame oil, miglyol, or the like.

In certain embodiments, injectable liquids may be used that, upon injection, undergo a phase transition and are transformed in situ into gel delivery vehicles. In certain embodiments, at least one polymer in the inner core may convert from a drug-containing liquid phase to a drug-infused gel phase upon exposure to a physiological fluid. Technologies based on in situ gelling compositions are described in U.S. Pat. Nos. 4,938,763, 5,077,049, 5,278,202, 5,324,519, and 5,780,044, all of which may be adapted to the present invention, and the disclosure of each is incorporated herein by reference.

In certain embodiments, the agent may be covalently linked to a polyoxyethylene ether, wherein the covalent bonds are cleavable in vivo so as to release the agent. In certain embodiments, the agent is released in a sustained manner. Methods shown for forming and applying conjugate prodrugs (e.g., PEG—drug conjugates) are shown in U.S. Pat. No. 5,681,964 and in U.S. Provisional Application No. 60/539306, the specifications of which are incorporated by reference in their entirety herein.

In certain embodiments, the agent is a pegylated prodrug of another agent.

In certain embodiments the agent may be included in compounds having structure 1 below:

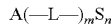

wherein A is a residue of a pharmaceutically active agent A', L represents a covalent bond or a linker moiety, and S is a polyoxyethylene ether group having the formula —$(OCH_2CH_2)_pOR$, where p is 2-12 and R is a $C_1$-$C_4$ alkyl group. The biocompatible fluid may comprise a mixture of compounds having a range of values of p; but in preferred embodiments p has a single value and the composition comprises only one compound of structure 1. The bond or linker L is cleavable in vivo so as to release the active agent A'. The agent A' will typically feature one or more functional groups to which linkers L can be readily attached. Examples of such functional groups include but are not limited to —$CO_2H$, —$CONH_2$, —CHO, =O, —OH, —$NH_2$, and —SH groups.

Examples of bonds and linkages which are cleavable in vivo, either by hydrolysis or by enzyme catalysis, include but are not limited to esters, amides, carbamates, carbonates, orthoesters, cyclic ketals, thioesters, thioamides, thiocarbamates, thiocarbonates, xanthates, disulfides, and phosphate esters. Ester linkages, carbonate linkers, and/or amino acid linker moieties are preferred. Enzymatically cleavable linkers for polyoxyethylene derivatives have been described, for example, in U.S. Pat. No. 6,127,355, Ulbrich et al., *Makromol. Chem.* 1986; 187:1131-1144, Conover et al., and *Anti-Cancer Drug Design* 1999; 14:499-506, and in many of the references cited therein, and the use of such linkers is specifically contemplated. Ester linkages may also be used (see R. Bronaugh et al., *Percutaneous Absorption* 3rd Ed., p.58-63, R. L. Bronaugh and H. I. Maibach, eds., Marcel Dekker, New York, 1999).

The values of m and n will typically range from 1 to 4, although larger values are within the scope of the invention. Typically, the linker is divalent and m and n will have the same value, but multiple links to a single moiety S, as for example in a ketal or orthoester linkage, may be employed. Alternatively, multiple moieties S may be appended via a single linker L, for example by esterification of the agent A with a moiety such as —$C(=O)CH[(OCH_2CH_2)_pOR]_2$ or —$P(=O)[(OCH_2CH_2)_pOR]_2$. Where m>1 and/or n>1, each incidence of L and S may be the same or different.

The residue represented by A may be derived from any agent, including but not limited to steroids (preferably corticosteroids), retinoids, NSAIDs, vitamin D3 and vitamin D3 analogs, antibiotics, and antiviral agents. Other suitable agents include enzymes, peptides and other large molecules. In certain embodiments of this invention, all-trans retinoic acid is excluded from the residues represented by A, while in other embodiments retinoids are excluded from the residues represented by A.

Suitable steroids include but are not limited to androgenic and estrogenic steroid hormones, androgen receptor antagonists and 5-α-reductase inhibitors, and corticosteroids. Specific examples include but are not limited to alclometasone, clobetasol, fluocinolone, fluocortolone, diflucortolone, fluticasone, halcinonide, mometasone, prednisone, prednisolone, methylprednisolone, triamcinolone, betamethasone, and dexamethasone, and various esters and acetonides thereof.

Suitable retinoids include but are not limited to retinol, retinal, isotretinoin, acitretin, adapalene, tazarotene, and bexarotene.

Suitable NSAIDs include but are not limited to naproxen, suprofen, ketoprofen, ibuprofen, flurbiprofen, diclofenac, indomethacin, celecoxib, and rofecoxib.

Suitable vitamin D3 analogues include but are not limited to doxercalciferol, seocalcitol, calcipotriene, tacalcitol, calcitriol, ergocalciferol, and calcifediol.

Suitable antiviral agents include but are not limited to trifluridine, cidofovir, acyclovir, penciclovir, famciclovir, valcyclovir, gancyclovir, and docosanol. Suitable antibacterial agents include but are not limited to metronidazole, clindamycin, erythromycin, vancomycin, ciprofloxacin, ofloxacin, lomefloxacin, bacitracin, neomycin, mupirocin, and polymyxin B. The antiviral and antibacterial prodrugs of the invention may be used to treat appropriately responsive systemic infections.

The linker L is cleavable in vivo, meaning that the compound of the invention is hydrolyzed or otherwise cleaved, with or without enzymatic catalysis, so as to generate in situ the active agent.

Examples of suitable linkers include, but are not limited to, —$CH_2O$—, —$OCH_2O$—, —$C(=O)$—O—, —$OC(=O)$—O—, —$C(=O)$—$(CH_2)_{1-4}$—O—, and —$C(=O)$—$(CH_2)_{1-4}$—, —$C(=O)$—NH—, and —$C(=S)$—NH—. Descriptions of suitable linkers may be found in *Prodrugs: Topical and Ocular Drug Delivery*, 1992, K. B. Sloan (Ed.), Drugs and the Pharmaceutical Sciences, Vol 53 (Marcel Dekker). It will be appreciated that the rate of cleavage will vary depending on the precise structures of the active agent and the polyoxyethylene ether, and on the nature of the linker or bond L and the point(s) of attachment. The efficiency of prodrug cleavage of linkers for any specific embodiment can be readily determined by those of skill in the art; for a review of methods see A. Stichcomb, 2003, *Pharm Res.* 20:1113-1118.

The linker or bond L may be attached to any suitable heteroatom present in the topically active agent that carries an exchangeable hydrogen, such as —OH, SH, NH$_2$, and COOH groups. By way of example, the free hydroxyl group of triamcinolone acetonide may be acylated with the moiety —C(=O)(OCH$_2$CH$_2$)$_p$OR.

In one embodiment, the active agent comprises a carboxylic acid group, and the carboxylic acid group is esterified with a polyoxyethylene ether of formula HO(CH$_2$CH$_2$O)$_p$R. Examples include but are not limited to structures I, II, and III shown below:

I

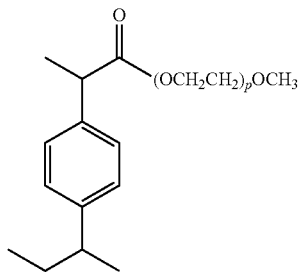

II

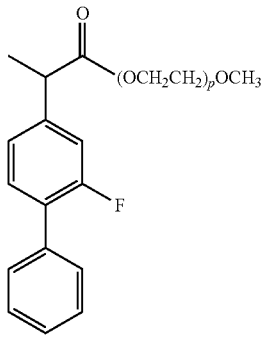

III

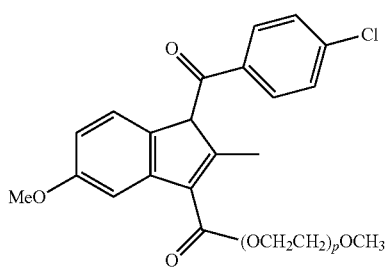

In an alternative embodiment, the active agent comprises a hydroxyl group, and the hydroxyl group is acylated with a polyoxyethylene ether carbonyl moiety of formula —CO(OCH$_2$CH$_2$)$_p$OR. Examples include but are not limited to structures IV and V shown below:

IV

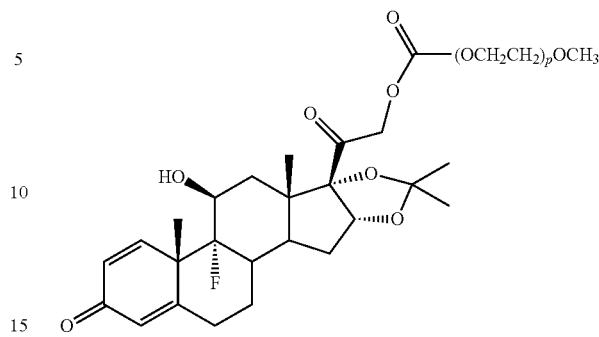

V

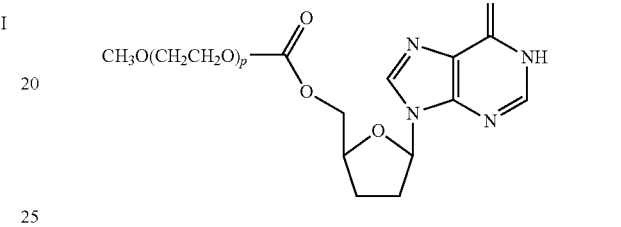

In certain embodiments, the biocompatible fluid includes a prodrug comprising a pharmaceutical compound linked to a polyoxyethylene ether moiety of the formula: —(OCH$_2$CH$_2$)$_p$ OR, wherein p=2-12 and R is a C$_1$-C$_4$ alkyl group. In certain embodiments, n is an integer from 2 to 6 inclusive. The identities of the group R may be methyl, ethyl, or any other organic moiety.

In certain embodiments, the use of prodrug linkages in connection with an agent may improve the solubility of an agent in water or in polymer. For example, the use of a pegylated prodrug may improve the solubility of an agent in the biocompatible fluid, and thereby improve the injectability of the invention. The use of prodrug linkages may also lower the melting point of a solid agent, or increase the solubility of an agent in physiological fluids, thereby improving the injectability of the agent.

The agent may be dissolved, dispersed or suspended in the biocompatible core, whereupon it may leach out of the core and into surrounding fluid. In certain embodiments, the agent may rapidly escape from an injection mixture after injection into a physiological system.

In certain embodiments, the biocompatible solid component may be, for example but without limitation, poly(lactic co-glycolic) acid (PLGA).

In certain embodiments the inner core is a viscous paste containing at least 10% agent, or preferably over 50% agent or, more preferably, over 75% agent.

In certain embodiments, the polymer system is injected or inserted into a physiological system (e.g., a patient). Upon injection or insertion, the delivery system will contact water or other immediately surrounding physiological fluid that will enter the polymer system and contact the inner core. In certain embodiments, the core materials may be selected so as to create a matrix that reduces (and thereby allows control of) the rate of release of the agent from the delivery system.

In preferred embodiments, the agent's rate of release from the system is limited primarily by the permeability or solubility of the agent in the matrix. However, the release rate may be controlled by various other properties or factors. For example, but without limitation, the release rate may be controlled by the size of the diffusion pore(s), the permeability of the second layer of the polymer system, the physical properties of the core (e.g., the permeability or solubility of an agent in the biocompatible solid as opposed to the permeability or solubility of the agent in the biocompatible fluid of the biocompatible core component), the dissolution rate of the core or components of the core, or the solubility of the agent in the physiological fluid immediately surrounding the polymer system.

In certain embodiments, the rate of release of the agent may be limited primarily by any of the foregoing properties. For example, in certain embodiments, the rate of release of the agent may be controlled, or even limited primarily by, the size of the diffusion pore(s). Depending on the desired delivery rate of the agent, the first layer may coat only a small portion of the surface area of the inner core for faster release rates of the agent (i.e., the diffusion pore(s) is relatively large), or may coat large portions of the surface area of the inner core for slower release rates of the agent (i.e., the diffusion pore(s) is relatively small).

For faster release rates, the first layer may coat up to about 10% of the surface area of the inner core. In certain embodiments, approximately 5-10% of the surface area of the inner core is coated with the first layer for faster release rates.

Certain embodiments may achieve desirable sustained release if the first layer covers at least 25% of the surface area of the inner core, preferably at least 50% of the surface area, more preferably at least 75%, or even greater than 85% or 95% of the surface area. In certain embodiments, particularly where the agent is readily soluble in both the polymer core and the biological fluid, optimal sustained release may be achieved if the first layer covers at least 95% or 99% of the inner core. Thus, any portion of the surface area of the inner core, up to but not including 100%, may be coated with a first coating layer to achieve the desired rate of release of the agent.

The first coating may be positioned anywhere on the inner core, including but not limited to the top, bottom or any side of the inner core. In addition, it could be on the top and a side, or the bottom and a side, or the top and the bottom, or on opposite sides or on any combination of the top, bottom or sides.

The composition of the first coating layer is selected so as to allow the above-described controlled release. The preferred composition of the first layer may vary depending on such factors as the active agent, the desired rate of release of the agent and the mode of administration. The identity of the active agent is important because its molecular size determines, at least in part, its rate of release into the second layer.

In certain embodiments, the release rate of the agent from the inner core may be reduced by the permeability of the second coating layer. In certain embodiments, the second layer is freely permeable to the agent. In certain embodiments, the second layer is semi-permeable to the agent. In certain embodiments, the agent has a permeability coefficient in the second coating layer of less than about $1 \times 10^{-10}$ cm/s. In other embodiments the permeability coefficient in the second coating layer is greater than $1 \times 10^{-10}$ cm/s, or even greater than $1 \times 10^{-7}$ cm/s. In certain embodiments the permeability coefficient is at least $1 \times 10^{-5}$ cm/s, or even at least $1 \times 10^{-3}$ cm/s, or at least $1 \times 10^{-2}$ cm/s in the second layer.

In certain embodiments, the agent has a permeability coefficient in the first coating layer of less than about $1 \times 10^{-10}$ cm/s. In other embodiments the permeability coefficient in the first coating layer is greater than $1 \times 10^{-10}$ cm/s, or even greater than $1 \times 10^{-7}$ cm/s. In certain embodiments the permeability coefficient is at least $1 \times 10^{-5}$ cm/s, or even at least $1 \times 10^{-3}$ cm/s, or at least $1 \times 10^{-2}$ cm/s in the first coating layer.

In certain embodiments, the inner core undergoes a phase change (i.e. the biocompatible solid precipitates) and converts to a gel upon implant or insertion of the polymer system in a physiological system. The phase change may reduce the rate of release of the agent from the inner core. For example, where at least part of the core is provided first as a liquid and converts to a gel, the gel phase of the polymer core may be less permeable to the agent than is the liquid phase of the polymer core prior to the conversion to the gel. In certain embodiments, the polymer core in gel phase is at least 10% or even at least 25% less permeable to the agent than is the liquid phase. In other embodiments, the precipitated biocompatible solid is at least 50% or even at least 75% less permeable to the agent than is the biocompatible fluid alone.

In certain embodiments, interaction of the core with the physiological fluid may alter the solubility of the agent in the core, and thereby reduce the release rate of the agent. For example, the core may be at least 10% or even at least 25% less solubilizing to the agent than before interaction with physiological fluid; in other embodiments, where a gel phase occurs, the gel phase is at least 50% or even at least 75% less solubilizing to the agent.

In certain embodiments, the biocompatible solid and/or biocompatible fluid components of the core may dissolve when in contact with physiological fluid. The rate at which such components dissolve may impact the rate of release of the agent. In certain embodiments, as the core component(s) erode or dissolve, the rate of release of the agent may increase. For example, in certain embodiments less than about 10% of the core component(s) may erode or dissolve over a period of about 6 hours. This may increase the rate of release of the agent by less than about 10% over that time. In certain embodiments, the biocompatible core component(s) may erode or dissolve more slowly (e.g. less than about 10% over a period of about 24 hours, or even over a period of multiple days, weeks, or even months). In certain embodiments, such erosion or dissolution may occur more rapidly (e.g. greater than about 10% over a period of about 6 hours, in certain embodiments even greater than 25% over a period of about 6 hours).

In certain embodiments, the solubility of the agent in the core impacts the rate of release of the agent from the polymer system. In certain embodiments, the agent is soluble, moderately soluble, or even slightly soluble or very slightly soluble in the core. The agent's release rate from the polymer core where an agent is soluble in the core exceeds the rate of release where the agent is only slightly or very slightly soluble in the polymer core.

In certain embodiments, the release rate of the agent from the inner core may be controlled by the ratio of the agent to the biocompatible solid component of the core (also referred to as the "drug loading"). By changing the drug loading, different release rate profiles can be obtained. Increasing the drug loading may increase the release rate. For a slower release profile, drug loading may be less than 10%, and preferably less than 5%. For a faster release profile, drug loading may be more than 10%, and preferably more than 20%, or even greater than 50%.

In certain embodiments, the agent may have low solubility in the physiological fluid immediately surrounding the implanted/inserted polymer system. In such embodiments, the rate of release of the agent from the polymer system may be controlled by the solubility of the agent in such surrounding fluid (i.e., the lower the solubility of the agent in the immediately surrounding fluid the lower its rate of release from the polymer system). In certain embodiments, the solubility of the agent in the surrounding physiological fluid is moderate or less.

In certain embodiments, the agent is a codrug, or a prodrug thereof, wherein the codrug or prodrug thereof is at least 5% less soluble in the surrounding physiological fluid than are its constituent components. In such embodiments, the rate of release of the agent may be at least 5% less than the rate of release of the unlinked constituents from the polymer system. In certain embodiments, the codrug or prodrug thereof is at least 10%, even at least 25%, at least 50%, or at least 75% less soluble in the surrounding fluid than are its unlinked constituents. The rate of release of the constituents may be reduced accordingly when provided in codrug (or prodrug thereof) form as compared to their unlinked forms. In certain embodiments using a codrug, the codrug disassociates upon contact with physiological fluid to generate and release one or more therapeutically active agents from the core.

Thus, the rate of release of the agent according to the invention may be limited primarily by any of the above properties or any other factor. For example, but without limitation, the release rate may be controlled by the size and/or location of the diffusion pore(s), the permeability or other properties of the first or a second layer in the polymer system, the physical properties of the core (e.g., a gel after a phase transition), the dissolution rate of one or more of the core components, the solubility of the agent within the core, the solubility of the agent in the physiological fluid immediately surrounding the polymer system, etc. In certain preferred embodiments, the release of the agent may be limited primarily by any one factor, such that the rate of release is lower as a result of that one factor. In certain embodiments, the rate of release of the agent is at least 10% slower as a result of one factor than as a result of any other factor. In certain embodiments, the rate of release of the agent is at least 25%, or even at least 50% or at least 75% slower as a result of one factor than as a result of any other factor.

The foregoing factors are illustrative only. The skilled artisan will readily appreciate that any other property of the inventive system may be the limiting factor in the agent's release rate from the system.

In another aspect, the inventive system is provided in a drug delivery device capable of delivering one drug or even two or more synergistic drugs over a prolonged period. In certain embodiments, the inventive system provides sustained release of a therapeutically effective amount of an agent to a patient in need thereof. In preferred embodiments, the device allows delivery of the compounds over a period of at least 3 hours, preferably at least 12 hours, or even 1 day, at least 2 days, or even at least 1 week, at least 1 month, or at least 1 year. In some embodiments, the inventive system may be deployed on a stent or other device. Such devices include, but are not limited to surgical screws, prosthetic joints, artificial valves, plates, pacemakers, sutures, etc.

Definitions

The term "active" as used herein means biologically, therapeutically or pharmacologically active.

The term "agent" as used herein is synonymous with "at least one agent," "compound," or "at least one compound," and means at least one drug or codrug, or a prodrug thereof. In certain embodiments, the agent may be at least one low-solubility codrug, or a prodrug thereof. In certain embodiments the codrug, or prodrug thereof, is designed to have low solubility in either the core, the biological fluid or both. In certain embodiments, the agent may be a protein, peptide, or a pegylated agent. In still other embodiments, the term "agent" refers to a plurality of drugs, proteins, peptides, etc.

In certain embodiments the agent may be in granular form. In certain embodiments, the agent may be combined with a pharmaceutically acceptable carrier. In certain embodiments, the agent is in liquid form.

An "effective amount" of an agent, with respect to methods of treatment, refers to an amount of the agent in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose.

The term "$ED_{50}$" means the dose of a drug that produces 50% of its maximum response or effect.

The terms "granule," "particle," or "particulate" as used herein are used interchangeably and refer to any particle. In certain exemplary embodiments, the particles have a diameter in the range of about 0.01 mm to about 3 mm, preferably in the range of about 0.1 mm to about 2 mm, or even more preferably in the range of about 0.3 mm to about 1.5 mm.

As used herein, the term "$EC_{50}$" means the concentration of a drug that produces 50% of its maximum response or effect. The term "$IC_{50}$" means the dose of a drug that inhibits a biological activity by 50%.

The term "$LD_{50}$" means the dose of a drug that is lethal in 50% of test subjects.

The term "therapeutic index" refers to the therapeutic index of a drug defined as $LD_{50}/ED_{50}$.

A "patient" or "subject" to be treated by the inventive system refers to either a human or non-human animal.

"Physiological conditions" describe the conditions inside an organism, i.e., in vivo. Physiological conditions include the acidic and basic environments of body cavities and organs, enzymatic cleavage, metabolism, and other biological processes, and preferably refer to physiological conditions in a vertebrate, such as a mammal.

In general, "low solubility" means that the agent is only very slightly soluble in a medium (e.g., aqueous solutions having pH in the range of about 5 to about 8, and in particular to physiologic solutions, such as blood, blood plasma, etc., other relevant mediums include gels and other materials in the polymer core). Some agents, e.g., low-solubility agents, will have solubilities of less than about 1 mg/ml in the medium, less than about 100 μg/ml, preferably less than about 20 μg/ml, more preferably less than about 15 μg/ml, and even more preferably less than about 10 μg/ml. Solubility in water is measured at a temperature of 25° C. as measured by the procedures set forth in the 1995 USP, unless otherwise stated. According to the invention, compounds which are soluble (greater than about 100 mg/ml), moderately soluble (about 100 mg/ml to about 10 mg/ml), slightly soluble (about 10 mg/ml to about 1 mg/ml), very slightly soluble (about 1 mg/ml to about 0.1 mg/ml) and practically insoluble or insoluble compounds (less than about 0.1 mg/ml, preferably less than about 0.01 mg/ml) are contemplated.

As used herein, an agent's "LogP" refers to the logarithm of P (Partition Coefficient), where P is a measure of how the agent partitions between octanol and water. P itself is a constant, defined as the ratio of concentration of compound in aqueous phase to the concentration of compound in octanol according to the following:

Partition Coefficient, $P$=[Organic]/[Aqueous],
where [ ]=concentration $LogP$=$log_{10}$ (Partition Coefficient)=$log_{10}P$ A LogP value of 1 means that the concentration of the compound is ten times greater in the organic phase than in the aqueous phase. The increase in a LogP value of 1 indicates a ten-fold increase in the concentration of the compound in the organic phase as compared to the aqueous phase.

The term "residue" when applied to an agent means a part of an agent that is substantially identical to the agent from which it is derived, with minor differences arising by virtue of having one or more atoms removed to provide points of attachment for the linker(s) L. Typically, at least one functional group of the residue will be altered (relative to the parent pharmaceutically active agent) to accommodate the covalent linker. This will typically involve removal of an exchangeable hydrogen and/or a single heteroatom, leaving a free valence for attachment of the linkage L. For instance, where the agent includes a carboxylate functional group, the residue of the agent formed by removal of a hydroxyl group may form an ester bond with a hydroxyl group on a polyoxyethylene ether residue, which itself is formed by removal of a hydrogen atom from a hydroxyl group from the polyoxyethylene ether. In this sense, the term "residue" as used herein is analogous to the sense of the word as it is used in peptide and protein chemistry to refer to a residue of an amino acid in a peptide.

The terms "linker" and "linkage," which are used interchangeably herein, refer to a direct bond or to a multivalent group of atoms incorporating and connecting the functional groups of the active agent and a polyoxyethylene ether, which is metabolized under physiological conditions to release the active agent A'. In certain embodiments, the linker is a substantially linear moiety having no more than 25 atoms, more preferably less than 10 atoms. Preferred linkers are ones which, upon release of the topically active agent, and when further metabolized, generate byproducts that are non-toxic and inert at the effective dosing concentration. Direct bonds between the residue A and the polyoxyethylene moiety S are particularly preferred.

The term "codrug" as used herein means a compound comprising a first molecule residue associated with a second molecule residue, wherein each residue, in its separate form (e.g., in the absence of the association), is an active agent or a prodrug of an active agent. In preferred embodiments, either one or both of the first and second molecule residues are small molecules. The association between said residues can be either ionic or covalent and, in the case of covalent associations, either direct or indirect through a linker. The first molecule can be the same or different from the second. Exemplary formulae for codrugs can be seen in formulae I, Ia, II, IIa, III, IIIa, and IV:

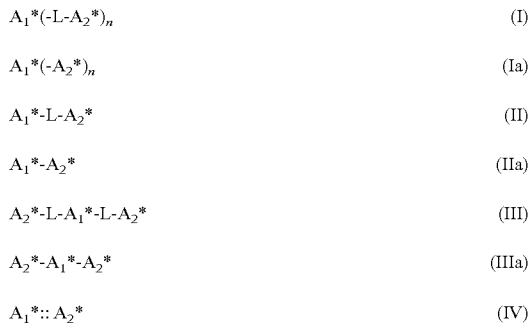

wherein each of $A_1^*$, $A_2^*$, and L are defined as follows:
$A_1^*$ is a residue of a first biologically active compound, $A_1$;
$A_2^*$ is a residue of a second biologically active compound, $A_2$, which may be the same as or different from $A_1$;
L is a linking group selected from a direct bond and a divalent organic linking group; and
n is an integer having a value of from 1 to 4, preferably 1; and :: is an ionic bond.

The term "prodrug" as used herein means a first residue associated with a second residue, wherein one of the residues is biologically active. In preferred embodiments, either one or both of the first and second residues are small molecules. In some embodiments, one of the residues is not biologically active; in some embodiments the prodrug may be biologically inactive in its prodrug form. The association between said residues is covalent and can be either direct or indirect through a linker. Prodrugs of biologically active compounds include esters, as well as anhydrides, amides, and carbamates that are hydrolyzed in biological fluids to produce the parent compounds. Those skilled in the art will realize that a "prodrug" is a moiety that is generally not pharmacologically active. However, when activated, typically in vivo by enzymatic or hydrolytic cleavage to convert the prodrug to an active biological moiety, the administration of the prodrug to the individual will have had the intended medical effect. Prodrugs are typically formed by chemical modification of a biologically active moiety. Conventional procedures for the selection and preparation of suitable prodrug derivatives are described, for example, in Design of Prodrugs, ed. H. Bundgaard, Elsevier, 1985."

The term "physiological pH," as used herein, refers to a pH that is about 7.4 at the standard physiological temperature of 37.4° C. The term "non-physiological pH," as used herein, refers to a pH that is less than or greater than "physiological pH," preferably between about 4 and 7.3, or greater than 7.5 and less than about 12. The term "neutral pH," as used herein, refers to a pH of about 7. In preferred embodiments, physiological pH refers to pH 7.4, and non-physiological pH refers to pH between about 6 and 7. The term "acidic pH" refers to a pH that is below pH 7, preferably below about pH 6, or even below about pH 4.

The term "bioerodible" is synonymous with "biodegradable" and is art-recognized. It includes polymers, compositions and formulations, such as those described herein, that degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, biodegradation may occur by enzymatic mediation, degradation in the presence of water and/or other chemical species in the body, or both.

The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction, in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

The phrase "pharmaceutically acceptable carrier" as used herein means a pharmaceutically acceptable material, composition or vehicle, such as a liquid or solid filter, diluent, excipient, solvent or encapsulating material, involved in carrying or transporting a subject drug from one organ, or portion of the body, to another organ, or portion of the body. Each carrier must be "acceptable" in the sense of being compatible with other ingredients of the formulation and not injurious to the patient.

Some examples of materials which can serve as pharmaceutically acceptable carriers include (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "protecting group" or "protective group" as used herein means a temporary substituent that protects a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

The term "residue" refers to that part of a compound that remains after the compound is linked, either directly to another compound by a direct bond or to a divalent linking moiety. For instance, where a residue Al comprises a carboxylic acid group that forms a linkage to a second residue $A_1$ through an amino group to form the compound $A_1$-$A_1$, including an amide linkage, the first residue $A_1$ is the residue of the parent compound that includes all of the parent except for the —OH that forms part of the amide group, while the other includes all of the parent except an H— from the amino group. A person having skill in the art will recognize that this is analogous to "residues" of amino acids in polypeptides and proteins, or to "residues" of ribonucleotides and deoxyribonucleotides in RNA and DNA, respectively.

According to the present invention, the phrase "limited primarily by" refers to the factor(s) associated with the rate-determining step in the release rate of an agent from the inventive system. For example, but without limitation, an agent's release rate is limited primarily by the rate of the agent's dissolution in the polymer where said rate of dissolution is the rate determining step in the release of the agent (e.g., said dissolution is slower than the rate of dispersion of the agent in the surrounding physiological fluid). Similarly, where the rate of release (e.g., the rate-determining step) is a result of the properties of the matrix (e.g., molecular weight, permeability in gel state to passage of the agent, size of the diffusion pore), the rate of release is also said to be "limited primarily by" such properties, such matrix, etc.

Exemplary Embodiments

In one embodiment, poly(lactic-co-glycolic acid) (PLGA) is dissolved in polyethylene glycol (PEG); the solution is kept in a 37° C. water bath. Equal amounts of the PLGA-PEG solution and bovine albumin are mixed and form a semi-solid gel. This gel is filled into a silicone cup (1.5mm ID) with a small hole in the bottom, and the top of the cup is then sealed with silicone adhesive. The hole in the bottom can be left open or coated with a polymer membrane to control the release. The finished assembly (silicone cup filled with Albumin-PGA-PEG gel) is placed in 0.1 m phosphate buffer (pH 7.4) at 37° C., and the release amount of albumin is analyzed using HPLC (FIG. 1).

The foregoing embodiment is presented for illustrative purposes only, and is not intended to be limiting. The person skilled in the art will recognize that additional embodiments according to the invention are contemplated as being within the scope of the foregoing generic disclosure, and no disclaimer is in any way intended by the foregoing, non-limiting examples.

All patents, publications, and references cited in the foregoing disclosure are expressly incorporated herein by reference.

The invention claimed is:

1. A drug delivery system comprising:
an inner core, comprising (i) a biocompatible fluid component consisting of polyethylene glycol, (ii) a biocompatible solid component dispersed, suspended, or dissolved in the biocompatible fluid component, wherein the biocompatible solid component is poly(dl-lactide-co-glycolide) and is more soluble in the biocompatible fluid component than in physiological fluid, and (iii) at least one agent dispersed, suspended, or dissolved within the inner core, wherein the inner core undergoes a phase change upon contact with a physiological fluid;
a first polymer layer, impermeable to the passage of the at least one agent, that covers at least part of but less than 100% of said inner core; and optionally, a second polymer layer that is permeable to the passage of the at least one agent; wherein the release rate of the agent is limited primarily by the portion of the inner core that is covered by the first polymer layer, the physical properties of the core, the dissolution rate of the core or components of the core, the permeability of the second polymer layer, or the solubility of the at least one agent in the physiological fluid immediately surrounding the polymer.

2. The drug delivery system of claim 1, wherein the first polymer layer covers at least about 50% of the inner core.

3. The drug delivery system of claim 1, wherein the inner core forms a gel upon contact with physiological fluid.

4. The drug delivery system of claim 3, wherein the at least one agent is at least 10% more soluble in the inner core in gel form than in the inner core prior to conversion to said gel.

5. The drug delivery system of claim 1, wherein, after contact with physiological fluid, the inner core is at least 10% less permeable to the agent than is the inner core prior to interaction with said fluid.

6. The drug delivery system of claim 1, wherein the at least one agent has a permeability coefficient in the second layer at least about $1 \times 10^{-5}$ cm/s but less than about $1 \times 10^{-2}$ cm/s.

7. The drug delivery system of claim 1, wherein the at least one agent has a release rate from the drug delivery system that is limited primarily by the permeability of the at least one agent in the inner core.

8. The drug delivery system according to claim 1, wherein the device is water-permeable.

9. The drug delivery system according to claim 1, wherein the inner core comprises a codrug or prodrug that is cleaved by water that permeates into the inner core.

10. The drug delivery device according to claim 1, wherein the at least one agent is a prodrug.

11. The drug delivery system of claim 10, wherein the at least one agent is covalently linked to a polyoxyethylene ether.

12. A drug delivery device, comprising:
the drug delivery system according to claim 1; and
a pharmaceutically acceptable carrier capable of delivering the at least one agent to a site within the body.

13. The drug delivery device of claim 12, wherein the at least one agent is a prodrug comprising an agent covalently linked to a polyoxyethylene ether.

14. A method of administering an agent to a patient in need thereof, comprising:
providing the drug delivery system according to claim 1, said system containing an effective amount of an agent suitable for treating the patient; and
administering the drug delivery system to the patient.

15. A method of manufacturing a drug delivery system, comprising: providing an inner core, said inner core comprising (i) a biocompatible solid component, (ii) a biocompatible fluid component consisting of polyethylene glycol, wherein the biocompatible solid is poly(dl-lactide-co-glycolide) and is more soluble in the biocompatible fluid than in physiological fluid, and (iii) at least one agent dispersed within said inner core; wherein the inner core undergoes a phase change upon contact with a physiological fluid; and combining said inner core with a first polymer layer that is impermeable to the at least one agent and covers at least part of but less than 100% of said inner core; and optionally, adding a second polymer layer that is permeable to the passage of the at least one agent; wherein the release rate of the agent is limited primarily by the portion of the inner core that is covered by the first polymer layer, the physical properties of the core, the dissolution rate of the core or components of the core, the permeability of the second polymer layer, or the solubility of the at least one agent in the physiological fluid immediately surrounding the polymer.

16. The method of claim 15, wherein the inner core and first polymer layer are combined by co-extrusion.

17. A medical device, comprising the drug delivery system according to claim 1 adapted to provide a drug to a patient in need thereof.

18. A drug delivery system of claim 1, wherein the first polymer layer is a formed of a material selected from polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene chlorinated polyethylene, poly(1,4-isopropylidene diphenylene carbonate), vinylidene chloride, acrylonitrile copolymer, vinyl-chloride-diethyl fumarate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, and vinylidene chloride-acrylonitride copolymer.

19. A drug delivery system of claim 18, wherein the first polymer layer is formed of a material selected from cross-linked polyvinyl alcohol, plasticized ethylene vinylacetate copolymer, polyvinyl alcohol, polymethylmethacrylate, plasticized nylon, plasticized soft nylon, silicone rubbers, and silicone-carbonate copolymers.

20. A method of claim 15, wherein the first polymer layer is formed of a material selected from polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene chlorinated polyethylene, poly(1,4-isopropylidene diphenylene carbonate), vinylidene chloride, acrylonitrile copolymer, vinyl-chloride-diethyl fumarate copolymer, silicone rubbers, medical grade polydimethylsiloxanes, ethylene-propylene rubber, silicone-carbonate copolymers, vinylidene chloride-vinyl chloride copolymer, vinyl chloride-acrylonitrile copolymer, and vinylidene chloride-acrylonitride copolymer.

21. A method of claim 20, wherein the first polymer layer is formed of a material selected from cross-linked polyvinyl alcohol, plasticized ethylene vinylacetate copolymer, polyvinyl alcohol, polymethylmethacrylate, plasticized nylon, plasticized soft nylon, silicone rubbers, and silicone-carbonate copolymers.

22. The drug delivery system of claim 1, wherein the at least one agent is a peptide or protein.

23. The method of claim 15, wherein the at least one agent is a peptide or protein.

* * * * *